United States Patent [19]

Hart et al.

[11] 4,375,571

[45] Mar. 1, 1983

[54] PROCESS FOR THE PREPARATION OF ETHYLBENZENE FROM 4-VINYLCYCLOHEXENE-1

[75] Inventors: Donald W. Hart; Lynn H. Slaugh, both of Houston, Tex.

[73] Assignee: Shell Oil Company, Houston, Tex.

[21] Appl. No.: 295,919

[22] Filed: Aug. 24, 1981

Related U.S. Application Data

[63] Continuation-in-part of Ser. No. 280,636, Jul. 6, 1981, abandoned.

[51] Int. Cl.$^3$ .................................................. C07C 5/03
[52] U.S. Cl. ...................................... 585/431; 252/475; 252/476; 585/412; 585/415; 585/440; 585/444
[58] Field of Search ............... 585/412, 415, 431, 440, 585/444; 252/475, 476

[56] References Cited

U.S. PATENT DOCUMENTS

| | | | |
|---|---|---|---|
| 2,438,041 | 3/1948 | Dutcher | 585/431 X |
| 2,771,495 | 11/1956 | Pines et al. | 585/431 |
| 2,804,489 | 8/1957 | Pines et al. | 585/431 X |
| 2,836,633 | 5/1958 | Esmay et al. | 252/447 X |
| 2,992,884 | 7/1961 | Bienstock et al. | 252/476 X |
| 3,903,185 | 9/1975 | Vogel et al. | 260/668 D |
| 4,029,715 | 6/1977 | Rieve et al. | 260/668 D |
| 4,048,243 | 9/1977 | Ruckelshauss | 585/431 |

FOREIGN PATENT DOCUMENTS

| | | | |
|---|---|---|---|
| 279614 | 11/1970 | U.S.S.R. | |
| 718449 | 2/1980 | U.S.S.R. | 585/444 |

*Primary Examiner*—Thomas A. Waltz

[57] ABSTRACT

4-Vinylcyclohexene-1 is converted to ethylbenzene by contacting the vinylcyclohexene at a temperature ranging from about 100° C. to about 450° C. with a catalyst prepared by impregnating an alumina with an oxide or decomposable salt of Na, K, Rb, Cs, Ca, Sr and/or Ba and calcining the impregnated material at a temperature ranging from about 450° C. to about 750° C.

11 Claims, No Drawings

PROCESS FOR THE PREPARATION OF ETHYLBENZENE FROM 4-VINYLCYCLOHEXENE-1

This application is a continuation-in-part of application Ser. No. 280,636, filed July 6, 1981, now abandoned.

FIELD OF THE INVENTION

This invention relates to a catalyst and a process for converting 4-vinylcyclohexene-1 to ethylbenzene.

BACKGROUND OF THE INVENTION

Ethylbenzene is a feedstock for the commercial preparation of styrene monomer. Commercially, ethylbenzene is made by alkylating benzene. Benzene, however, is expensive and routes to styrene utilizing a non-benzene feedstock would be economically desirable.

Butadiene is becoming increasingly available in economic amounts. A process route that would lead from butadiene to ethylbenzene and/or styrene would be quite useful. It is known in the literature to dimerize butadiene via the Diels-Alder reaction to 4-vinylcyclohexene. A catalyst that would effectively convert vinylcyclohexene to ethylbenzene and/or styrene would be very useful in a commercial process starting with butadiene and leading to styrene monomer. Catalysts are known for the conversion of vinylcyclohexene to ethylbenzene. See, for example, U.S. Pat. No. 3,903,185 issued Sept. 2, 1975 to Vogel et al, U.S. Pat. No. 4,029,715, issued June 14, 1977 to Rieve et al, and U.S.S.R. Pat. No. 279,614, issued Nov. 24, 1970 to Sterlitamak Chemical Works. Although the art teaches the use of potassium salts as promoters for Group VIII transition metal catalysts, the art does not teach the use of a potassium salt as a dehydrogenation catalyst per se. In fact, the art teaches that potassium salts supported on alumina are isomerization catalysts rather than dehydrogenation catalysts.

SUMMARY OF THE INVENTION

The instant invention provides for a process for converting 4-vinylcyclohexene-1 to ethylbenzene by contacting the 4-vinylcyclohexene at a temperature of about 100° C. to about 450° C. with a catalyst prepared by impregnating a porous alumina support with an oxide or a compound decomposable to an oxide upon calcination of a metal selected from the group consisting of sodium, potassium, rubidium, cesium, calcium, strontium, barium or mixtures thereof and subsequently calcining the resulting material at a temperature ranging from about 450° C. to about 750° C. The use of lithium and magnesium compounds do not provide the requisite activity. The use of other calcining temperatures are ineffective to produce an active catalyst for this dehydrogenation process. The porous alumina supports utilized have surface areas ranging from about 1 to about 500 m²/gm, preferably from about 50 to about 400 m²/gm. The supports are preferably gamma alumina. The siliceous supports do not provide for active catalysts. The instant catalyst provides several advantages over the prior art. The catalyst is relatively simple to make and does not require expensive Group VIII components to provide for activity. It provides a very high selectivity of ethylbenzene down to comparatively low temperatures when compared to prior art catalysts.

DESCRIPTION OF THE PREFERRED EMBODIMENTS

The catalysts utilized in the instant invention are prepared for example, by impregnating or otherwise providing a porous alumina support with a metal oxide or metal compound decomposable upon calcination to the oxide where the metal is selected from the group consisting of sodium, potassium, rubidium, cesium, calcium, strontium, barium or mixtures thereof and then calcining the resultant composition at a temperature ranging from about 450° C. to about 750° C., preferably from about 500° C. to about 700° C. Catalysts calcined below the desired lower temperature limits are not active. Calcining above the desired upper temperature limits results in excessive sintering with a resultant degradation of catalyst properties. It is thought that the metal oxide(s) or decomposable compound(s) during the calcination react after intermediate oxide formation with the alumina to form a metal aluminate. The catalyst preparation requires specific use of the metal oxide or compounds enumerated. The use of lithium and magnesium oxides or decomposable compounds do not provide the requisite activity. The calcination is carried out in any atmosphere: vacuum, reducing, neutral or oxidizing. Oxygen, in many cases can contaminate feedstocks, so that when an oxygen-containing gas is used for calcination, it is frequently advantageous to carry out the latter stages of calcination in neutral or reducing atmospheres in order to sweep out any oxygen from the catalyst material. When the decomposable compound has an organic anionic moiety such as carboxylate, alkoxylate, chelate, etc., it is preferred to carry out the calcining in a neutral atmosphere such as nitrogen or argon, or an oxidizing atmosphere such as air or oxygen. Calcining times are not critical and depend on calcining temperatures, higher temperatures requiring shorter times and vice versa. Typical times range from about 0.1 to about 50 hours. The time-temperature combination selected should be such that the metal oxide or decomposable compound carbonate reacts almost completely with the alumina. The metal compounds that are used to include, for example, carbonates, bicarbonates, hydroxides, chelates, alkoxylates and salts of other weak acids or salts of strong acids that decompose upon calcination such as the nitrates.

The alumina employed can be any of the variety of available aluminas or alumina hydrates, such as alumina gel, activated alumina, gamma alumina, etc. Regarding purity of the alumina, it may be stated that small amounts of impurities are not generally detrimental. The most suitable aluminas for use in the present invention are found to be those having surface areas ranging from about 1 to about 500 m²/gm, preferably from about 50 to about 400 m²/gm. Gamma alumina is a preferred support. Aluminas are readily available commercially which are readily usable in the instant invention. The following table lists several commercial gamma aluminas and their properties which are found suitable.

| Alumina | Surface Area, m²/g | Pore Vol., Co/gm | Na, ppm | $SO_4^=$, % wt | $Fe_2O_3$, % wt | $Cl^-$, % wt |
|---|---|---|---|---|---|---|
| CCI[a] | 252 | 0.8 | 160 | 0.06 | — | 0.02 |
| KA-201[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |

-continued

| Alumina | Surface Area, m²/g | Pore Vol., Co/gm | Na, ppm | $SO_4^=$, % wt | $Fe_2O_3$, % wt | $Cl^-$, % wt |
|---|---|---|---|---|---|---|
| Norton | 218 | 0.62 | 0.51 | 0.03 | — | 0.03 |
| CATAPAL[e] | 348 | 0.91 | | | | |
| FILTROL[f] | 214 | 0.82 | | | | |
| SCS 59[g] | 84 | 0.6 | | | | |

[a] Catalysts & Chemicals, Inc., now United Catalysts
[b] Kaiser
[c] Reynolds Corp.
[d] American Cyanamid Corp.
[e] Conoco Corp.
[f] Filtrol Corp.
[g] Pechiney-Saint Gobain Known methods for adding the metal oxide or decomposable compound to the alumina can be employed. A preferred method is to soak the alumina support pellets in an aqueous solution of the decomposable metal compound(s), drying the impregnated alumina, and then calcining at temperatures from about 450° C. to about 750° C., preferably from about 500° C. to 700° C. Dry impregnation can be suitably used. Since the metal oxide or decomposable compound is primarily reacting with the surface of the alumina, both external and internal pore surface, then the maximum amount of impregnating compound that can be effectively utilized will depend on the surface area. Of course, lesser amounts can be used. Ordinarily, the molar ratio of metal added to alumina will range from about 2:1 to about 1:50, preferably from about 1:1 to about 1:25. More preferably, the weight of the metal oxide or decomposable compound added will range from about 0.1 to about 30, even more preferably from about 1 to about 25, yet even more preferably, from about 2 to about 20 percent by weight measured as the metal. In a preferred embodiment a given portion of alumina pellets is impregnated with just sufficient amount of aqueous solution of decomposable metal compound to fill the pore volume of the alumina, then dried at temperatures ranging up to about 125° C., and then calcined at the requisite temperatures.

The catalyst is used in the typical fashion. Preferably, it is used in a fixed bed mode of operation, although fluidized beds and batch reactors can also be suitably used. In a typical illustrative embodiment, the catalyst is fixed in a fixed bed column and the feed vinylcyclohexene is heated to the reaction temperature and passed through the catalyst bed at the reaction temperature which ranges preferably from about 75° C. to about 450° C. The exit material is cooled and the product ethylbenzene is separated from the reactor products.

The instant invention thus comprises a catalyst for dehydrogenating 4-vinylcyclohexene to ethylbenzene at a temperature of about 100° C. to about 450° C. wherein said catalyst is prepared by impregnating a porous alumina support with an oxide or a compound decomposable to an oxide upon calcination of a metal selected from the group consisting of sodium, potassium, rubidium, cesium, calcium, strontium, barium or mixtures thereof and subsequently calcining the impregnated alumina at a temperature ranging from about 450° C. to about 750° C. It further encompasses the process for dehydrogenating 4-vinylcyclohexene to ethylbenzene which comprises contacting the 4-vinylcyclohexene at about 100°–450° C. with said catalyst.

The catalyst and process of this invention is illustrated by the following examples which are provided for illustration and comparative purposes and are not to be construed as limiting the invention.

ILLUSTRATIVE EMBODIMENTS

Catalyst Preparation

The following example typifies the preparation of the catalysts of the instant invention.

10 Grams of anhydrous $K_2CO_3$ are dissolved in 25 milliliters of deionized water. This solution is poured on 40 grams of Kaiser grade KA-201 alumina (20–30 mesh) while the latter is being stirred. The volume of the solution and the weight of the alumina are proportioned essentially to fill the pores in the alumina without excess solution remaining after impregnation. The impregnated material is dried at 60° C. for 1 hour. The dried material is then placed in a one inch quartz tube and nitrogen at a flow rate of 300 milliliters per minute is passed over the catalyst. The catalyst is then calcined by heating to 570° C. at 100° C. per hour heating rate and held at 575° C. for 16 hours. After cooling, the catalyst is stored in a nitrogen atmosphere. Analysis indicated that the composition contains about 12 percent by weight of potassium measured as the potassium metal.

Ethylbenzene Process

The following example illustrates the use of potassium carbonate/alumina as a catalyst for converting 4-vinylcyclohexene-1 to ethylbenzene.

A quartz reactor having a dimension of about 13 inches in length by about one-half inch in diameter is filled with 10 milliliters of the alumina composition prepared as described above. 4-Vinylcyclohexene is pumped into the reactor in a downflow mode at a liquid hourly space velocity of about 3 with the reaction temperature of the reactor being varied from about 100° C. to about 550° C. The product is analyzed using gas chromatography of the liquid product and the results are given in Table I below as a function of ethylbenzene selectivity at various reaction temperatures.

TABLE I

Dehydrogenation of 4-Vinylcyclohexene

| Temp. °C. | Conversion mol % | Mol % Selectivity Ethylbenzene | Styrene | Light Ends* |
|---|---|---|---|---|
| 100 | 100 | 100 | — | — |
| 130 | 100 | 100 | — | — |
| 300 | 100 | 99.9 | 0 | 0 |
| 350 | 100 | 99.7 | 0 | 0.2 |
| 400 | 100 | 97.4 | 0 | 1.6 |
| 453 | 100 | 88.1 | 3.7 | 8.1 |
| 500 | 100 | 61.7 | 20.6 | 15 |
| 550 | 100 | 10.2 | 27 | 36 |

*Light ends consists mostly of butadiene with minor amounts of benzene, toluene and other unidentified products present.

COMPARATIVE EXAMPLES

A series of catalysts both in accord and not in accord with this invention were prepared and tested by the techniques described above. The results are shown in Table II below. The precursor salts used to prepare the catalyst are shown in column 2 and the supports utilized in column 4. The last two columns give the mol % of 4-vinylcyclohexene converted and the selectivity to ethylbenzene.

TABLE II

Dehydrogenation of 4-Vinylcyclohexene

| Example | Salt | Metal, % wt. | Support | °C. Temp. | LHSV | Conv. 4-VCH | Selec. to EB |
|---|---|---|---|---|---|---|---|
| II-1 | LiNO$_3$ | Li 1.3 | KA-201[a] | 120 | 0.44 | 0 | — |
| II-2 | LiNO$_3$ | Li 4.9 | KA-201 | 120 | 1.74 | 0 | — |
| II-3 | K$_2$CO$_3$ | K 12.1 | KA-201 | 120 | 1.74 | 100 | 97.7 |
| II-4 | CsHCO$_3$ | Cs 14.5 | KA-201 | 120 | 1.74 | 100 | 98.3 |
| II-5 | Rb Acetate | Rb 12.7 | KA-201 | 120 | 1.74 | 100 | 98.7 |
| II-6 | Ca(NO$_3$)$_2$ | Ca 8.8 | KA-201 | 120 | 1.74 | 2.2 | 26 |
| II-7 | Mg(NO$_3$)$_2$ | Mg 2.3 | KA-201 | 120 | 1.74 | low | 0 |
| II-8 | Na$_2$CO$_3$ | Na 9.5 | KA-201 | 120 | 1.74 | 99.8 | 97.2 |
| II-9 | K$_2$CO$_3$ | K 8.85 | KA-201 | 120 | 1.74 | 99.8 | 96.3 |
| II-10 | KCO$_3$ | K 4.04 | KA-201 | 120 | 1.74 | 84.9 | 35.5 |
| II-11 | KOH | K 14.4 | KA-201 | 120 | 1.74 | 100 | 97.4 |
| II-12 | Ba(OH)$_2$ | Ba 9.7 | KA-201 | 120 | 1.74 | 100 | 92.9 |
| II-13 | K$_2$CO$_3$ | K 12.1 | KA-201 | 25 | 1.74 | 62.1 | 8.7 |
|  |  |  |  | 45 |  | 68.9 | 12.3 |
|  |  |  |  | 85 |  | 78.8 | 24.9 |
|  |  |  |  | 105 |  | 99.5 | 81.5 |
|  |  |  |  | 120 |  | 100 | 91.8 |
| II-14 | K$_2$CO$_3$ | K 12.1 | KA-201 | 120 | 1.74 | 100 | 94.0 |
|  |  |  |  | 90 |  | 99.8 | 89.5 |
|  |  |  |  | 75 |  | 94.1 | 61.1 |
| II-15 |  | K 12.1 | Type 57[b] | 120 | 1.74 | 0 | — |
| II-16 |  | K 4.04 | SCS 59[c] | 120 | 1.74 | 100 | 97.9 |
| II-17 |  | K 1.35 | SCS 59 | 120 | 1.74 | 53.4 | 15.7 |
| II-18 |  | K 12.1 | SCS 59 | 120 | 1.74 | 100 | 95.6 |
| II-19 |  | K 2.70 | SCS 59 | 120 | 1.74 | 100 | 97.4 |
| II-20 |  | K 2.70 | SCS 9[d] | 120 | 1.74 | 35.9 | 75.9 |
| II-21 |  | K 1.35 | SCS 9 | 120 | 1.74 | 0 | — |
| II-22 |  | K 5.4 | SCS 9 | 120 | 1.74 | 79.1 | 80.1 |

[a]Gamma alumina, manufactured by Kaiser, surface area about 365 m$^2$/gm
[b]Silica gel, manufactured by Davison Chemical Div., W. R. Grace & Co., surface area about 300 m$^2$/gm
[c]Gamma alumina, manufactured by Pechiney-Saint.Gobain, surface area about 84 m$^2$/gm
[d]Alpha alumina, manufactured by Pechiney-Saint.Gobain, surface area about 12 m$^2$/gm As can be seen from the above table, the use of lithium and magnesium salts (Examples II-1, II-2 and II-7) do not produce active catalysts. Silica, when used as a support (Example II-15) also does not produce an active catalyst.

When a comparative catalyst is prepared using potassium carbonate and which is calcined at about 400° C. and is tested as described above at a temperature of about 120° C., no dehydrogenation of vinylcyclohexene to ethylbenzene is observed, thus demonstrating the criticality of the calcining temperature. Catalysts calcined at, for example, 900° C. will show excessive sintering and a loss in selectivity.

We claim:

1. A process for dehydrogenating 4-vinylcyclohexene to ethylbenzene which comprises contacting the 4-vinylcyclohexene at a temperature of about 100° C. to about 450° C. with a catalyst prepared by impregnating a porous alumina support with an oxide or a compound decomposable to an oxide upon calcination of a metal selected from the group consisting of sodium, potassium, rubidium, cesium, calcium, strontium, barium or mixtures thereof and subsequently calcining the impregnated alumina at a temperature ranging from about 450° C. to about 750° C.

2. The process of claim 1 wherein the catalyst is calcined at a temperature ranging from about 500° C. to about 700° C.

3. The process of claim 1 or 2 wherein the metal oxide or compound added to the alumina support ranges from about 0.1 to about 30 percent by weight measured as the metal.

4. The process of claim 1 or 2 wherein the metal oxide or compound added to the alumina support ranges from about 1 to about 25 percent by weight measured as the metal.

5. The process of claim 1 or 2 wherein the metal oxide or compound added to the alumina support ranges from about 2 to about 20 percent by weight measured as the metal.

6. The process of claim 1 or 2 wherein the metal oxide or compound added to the alumina support is selected from the group consisting of sodium, potassium, rubidium, cesium or mixtures thereof.

7. The process of claim 1 or 2 wherein the metal oxide or compound added to the alumina support is selected from the group consisting of sodium, potassium or mixtures thereof.

8. The process of claim 1 or 2 wherein the metal oxide or compound added to the alumina support is selected from the group consisting of calcium, strontium, barium or mixtures thereof.

9. The process of claim 1 or 2 wherein the alumina support has a surface area ranging from about 1 to about 500 m$^2$/gm.

10. The process of claim 1 or 2 wherein the alumina support has a surface area ranging from about 50 to about 400 m$^2$/gm.

11. The process of claim 1 or 2 wherein the support is a gamma alumina with a surface area ranging from about 50 to about 400 m$^2$/gm.

* * * * *